United States Patent [19]

Delcour et al.

[11] Patent Number: 4,745,065

[45] Date of Patent: May 17, 1988

[54] GENES CONFERRING ON YEASTS A RESISTANCE TO HERBICIDES

[75] Inventors: Jean M. A. G. Delcour, Wahlin; Anne-Marie J. C. G. Colson-Corbisier, Thion-Valmon; Annie F. J. De Baetselier-van Broekhoven, Berchem; Charles Colson, Thion-Valmon, all of Belgium

[73] Assignee: Labofina, S.A., Brussels, Belgium

[21] Appl. No.: 608,162

[22] Filed: May 8, 1984

[30] Foreign Application Priority Data

May 9, 1983 [LU] Luxembourg .......................... 84795

[51] Int. Cl.$^4$ .................. C12N 15/00; C12N 5/00; C12N 7/00
[52] U.S. Cl. .................................. 435/256; 435/255; 435/172.1; 435/172.3; 435/317.1; 935/28; 935/69
[58] Field of Search ............. 435/240, 241, 172.3, 435/255, 256, 317; 935/28, 69

[56] References Cited

U.S. PATENT DOCUMENTS 4,443,971 4/1984 Chaleff ............................ 47/58

OTHER PUBLICATIONS

Dumas et al. 1984 "Molecular Cloning and DNA Sequence of the Yeast ILV2 Gene" (Abstract) *Am Soc. Microbiol Abstracts of Ann Meeting.*

Hinnen et al. 1978 "Transformation of Yeast" *Proc. Natl. Acad. Sci.* vol. 75, pp. 1929–1933.

Jimenez et al. 1980 "Expression of a Transposable Antibiotic Resistance Element in *Saccharomyces*" *Nature* vol. 287, 869–871.

Falco et al. 1985 "Genetic Analysis of Mutants of *Saccharomyces ceruisiae* resitant to the Herbicide Sulfometuron Methyl" *Genetics* vol. 109, 21–35.

Stalker et al. 1985 "A Single Amino Acid Substitution in the enzyme 5–Enolpyrulvylshikimate–3–Phosphate Synthase . . . *J. Biol. Chem.* vol. 260(8) 4724–4728.

Hirschberg et al. 1983 "Molecular Basis of Herbicide Resistance in *Amaranthus hybridus*", *Science* vol. 222 1346–1348.

Hughes 1983 "Selection for Herbicide Resistance" in *Handbook of Plant Cell Culture* vol. 1 Evans et al. (Eds) pp. 422–460.

Rogers, S. G., "Genetically Engineered Glyophosphate Tolerance in *E. Coli*", *J. Cell Biochem Suppl.* 713: 1213, p. 268, 1983.

*Primary Examiner*—Thomas G. Wiseman
*Assistant Examiner*—Robin Lyn Teskin
*Attorney, Agent, or Firm*—Stephen A. Bent; John K. Abokhair; M. Norwood Cheairs

[57] ABSTRACT

Disclosed is an autoreplicative plasmid containing DNA which encodes herbicide resistance, such that the plasmid is capable of transforming a yeast cell to become resistant to one or more organic herbicide growth inhibitors. Also disclosed is a process for the selective culture of yeasts transformed by the plasmid.

30 Claims, No Drawings

GENES CONFERRING ON YEASTS A RESISTANCE TO HERBICIDES

BACKGROUND OF THE INVENTION

The present invention relates to a gene conferring on a yeast, after transformation of the yeast cell, resistance to a herbicide-type growth inhibitor. More particularly, it concerns a plasmid wherein such a gene has been inserted in order to render a yeast cell transformed by the plasmid intrinsically resistant to the growth inhibitor. The invention also relates to a yeast made resistant to a herbicide-type growth inhibitor by transformation with such a plasmid. The present invention further concerns a process for the selective culture of yeast transformed by a plasmid containing a gene encoding resistance to a herbicide-type growth inhibitor.

It is known in the art to reprogram microorganisms genetically by transforming them with exogenous DNA under conditions that permit the DNA to replicate in the transformed cells, whereby the DNA is transmitted to the cells' progeny. The practical utility of these techniques is particularly evident when the exogenous DNA comprises at least one gene ensuring the expression by the transformed cell of a commercially valuable polypeptide, which could be either a hormone for medical use, like insulin, or an enzyme for industrial use, like amylase. Microorganisms thus transformed can be cultivated under suitable conditions so that they produce the polypeptide, which may then be recovered either from the microorganisms themselves or from the culture medium, depending on whether the polypeptide remains within the cultured cells or is excreted.

A laboratory method which is commonly used to transform a microorganism consists in using, as a vector for the exogenous gene of interest, an autoreplicating plasmid, i.e., a circular DNA molecule containing a sequence that makes it a replicon in the host cell. This plasmid also must contain at least one restriction site, i.e., a sequence specifically cleavable by a restriction enzyme.

If the plasmid once cleaved at a restriction site is the linked together with DNA fragments obtained either by excision from exogenous DNA or by in vitro synthesis, it is possible, using known techniques, to obtain so-called "chimeric" plasmids in which a fragment of exogenous DNA is inserted at the restriction site. After incubating a microorganism population in the presence of a DNA preparation containing such plasmids, it is possible to select from the population clones which have acquired, by transformation, one or more of the chimeric plasmids. The bank of clones thus obtained can then be screened in order to identify the one or several clones whose genome has been reprogramed by the DNA linked to the plasmid. Those clones are recognized either because they possess a new phenotypical feature which can easily be displayed by a culture on an indicator or selective medium, or because they respond positively to a test based on the use either of specific molecular probes, such as nucleic acids complementary to the gene sought, or of antibodies directed against the polypeptide encoded by the gene.

After identifying the clones sought, a fermentation process has to be developed which ensures an optimum production of the polypeptide of interest. In order to achieve this goal, two complementary approaches are usually applied: on the one hand, the chimeric vector is subjected to various in vitro manipulations in order to confer to the coding part of the corresponding gene a set of sequences best ensuring its expression; on the other hand, those culture conditions are selected which are best suited to the survival and proliferation of the transformed microorganisms, and to the exclusion of phenotypical revertants which might appear during fermentation. When such culture conditions have been defined, the fermentation process is genetically stable, and it can be used on an industrial scale.

It is known that the transformation of a microorganism according to the above methods most often produces an unstable transformant. The appearance of a growing proportion of phenotypically revertant cells in successive generations cultivated in a non-selective culture medium is a result of this unstability. An analysis above shows that such revertants have lost most or all of their plasmids (see K. Nagahari, *J. Bacteriol.* 136: 312, 1978). This situation results from the combination of two phenomena:

1. Spontaneous appearance within the culture of microorganisms partially or totally cured.
   This curing can result from several causes:
   statistical segregation of the plasmids during the cellular division;
   uncoupling of the replication of the plasmids and of the chromosomes;
   replication disadvantage of chimeric plasmids over endogenous plasmids (see C. P. Hollenberg, *Curr. Top. Microbiol. Immunol.* 96: 119, 1982).
2. Preferential proliferation of totally or partially cured microorganisms due to a selective disadvantage against the transformants (see K. Sakaguchi, in MOLECULAR BREEDING AND GENETICS OF APPLIED MICRO-ORGANISMS 1, Academic Press (ed. K. Sakaguchi & M. Okanishi 1980)).

This disadvantage is more pronounced when the expression of the genes contained in the plasmid is intense and requires a larger portion of cellular energy expenditures. This situation is paradoxical, since those wishing to develop a commercially viable process of industrial fermentation are primarily interested in maximizing expression of the cloned genes.

It is therefore necessary, in order to control the genetic stability of the population of microorganisms during fermentation, to exert an artificial selection pressure in favor of the transformants. This pressure can be exerted by adding to the culture medium a growth inhibitor towards which the vector-plasmid contains an extrinsic resistance marker. Most of the vectors used for the genetic manipulation of prokaryotic microorganisms confer on transformants a resistance to various antibiotics like ampicillin (inactivated by a β-lactamase), neomycin (inactivated by a phosphorylase), and chloramphenicol (inactivated by an acetylase).

The selection pressure can also be exerted by carrying out the fermentation in an artificial culture medium devoid of an essential metabolite, the de novo synthesis of which is catalyzed by an enzyme encoded by a gene carried exclusively by the vector, the corresponding allele carried by the chromosome of the host having been inactivated by mutation. This approach is particularly applicable to yeast cells, which by transformation, using the most commonly used vectors can acquire the ability to grow in a medium free of leucine (pJDB207), of tryptophan (YRp7), or of uracil (pFL1).

Stability control generally constitutes no serious handicap for the setting up of small-scale industrial fermentation processes, such as those developed for the manufacture of medically useful products with very high added value, like hormones or vaccines. No major cost or supply problem arises with the first type of selection, while the use of an artificial culture medium with the second type of selection is acceptable from either a technical or an economical point of view; in either case, the amounts of product required remain relatively limited.

However, the need to resort to such practices considerably limits the prospects for setting up large scale industrial fermentation processes, such as those for the manufacture of large amounts of products with relatively low added value, such as certain enzymes with food processing use which are produced by transformed yeast. In this case, the use of artificial media devoid of an essential metabolite which the phenotypic revertants (as opposed to the transformants) are incapable of synthesizing, is particularly disadvantageous in light of the difficulty of preparing these media and their prohibitive prices.

On the other hand, the use of natural culture media which are relatively abundant and inexpensive, like lactoserum or molasses, has heretofore proven totally unworkable; such media are by nature non-selective because of their relatively high content of essential metabolites. In media of this type, the addition of significant amounts of antibiotics, such as chloramphenicol or a derivative of neomycin known as G418, an extrinsic resistance to which has been imparted to yeast by transformation (see C. P. Hollenberg, *ICN-UCLA Symp. Mol. Cell. Biol.* 15: 135, 1979; A. Jimenez & J. Davies, *Nature* 287: 869, 1980), would not only increase the fermentation costs significantly but would also entail serious supplying difficulties for those molecules for which the principal use was medical or veterinary. It is also known that yeast cells, like the cells of other eukaryots, are indifferent to most of the currently available antibiotics; it is deemed very unlikely, therefore, that other resistance markers to antibiotic-type inhibitors will be discovered for yeast and be profitably used to control stability in an efficient manner.

SUMMARY OF THE INVENTION

An object of the present invention, therefore, is to provide a gene which, after transformation of a yeast cell by means of an autoreplicative plasmid containing the gene, imparts to the yeast an intrinsic resistance to one or several growth inhibitors of the synthetic organic herbicide type. Such inhibitors, unlike antibiotics, have the advantage of being abundant and inexpensive.

Another object of the present invention is to provide a plasmid containing the above-described gene, which plasmid can be used for transforming yeast cells under such conditions as to secure the replication and transmission of the gene to the cells' progeny, as well as the expression by the transformed yeast cells of the resistance trait encoded by the gene.

Still another object of the present invention is to provide a yeast which is made resistant to at least one synthetic organic herbicide by transformation with a plasmid of the type as hereabove described.

A further object of the present invention is to provide a process which allows at an industrial scale a genetically stable fermentation of yeast transformed with such a plasmid.

In accomplishing the foregoing objects, there has been provided in accordance with the present invention a recombinant yeast cloning vector comprising (i) a plasmid capable of autonomous replication in a yeast cell and (ii) DNA coding for resistance to at least one organic herbicide. In one preferred embodiment of the present invention, the DNA contained in the cloning vector codes for resistance to a herbicide of the formula

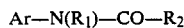

wherein
Ar is a radical including a ring having an aromatic character
$R_1$ is selected from the group consisting of a hydrogen, methyl radical and an hydroxyl radical, and
$R_2$ is a radical selected from the group consisting of an alkyl, a cycloalkyl, an alkenyl, an alkylamino, a cycloalkylamino, a dialkylamino, a methoxymethylamino and a alkoxy radical.

In another preferred embodiment of the present invention, the DNA contained in the cloning vector encodes a resistance to a herbicide having the following formula:

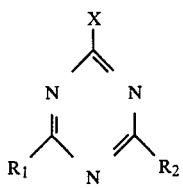

wherein
X is a radical selected from the group consisting of a chloro, a methoxy and a methylthio radical, and
$R_1$ and $R_2$, which may be identical or different, are radicals selected from the group consisting of a ethylamino radical and, isopropylamino radical.

According to another aspect of the present invention, there has been provided a yeast culture comprised of yeast transformants containing a yeast cloning vector comprising (i) a plasmid capable of autonomous replication in a yeast cell and (ii) DNA coding for resistance to at least one organic herbicide.

According to another aspect of the present invention, there has been provided a process for the culturing of yeast, comprising the step of maintaining a yeast culture comprised of yeast transformants containing a yeast cloning vector comprising (i) a plasmid capable of autonomous replication in a yeast cell and (ii) DNA coding for resistance to at least one organic herbicide on on a growth medium which comprises, as the sole carbon source for said culture, a substrate for respiration, said medium containing an amount of an organic herbicide to which said transformants are resistant which is sufficient to keep said culture substantially free of revertants.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF PREFERRED EMBODIMENTS

As an important aspect of the present invention, it has been unexpectedly found that yeast growth is inhibited by numerous synthetic chemical products currently used as total or selective herbicides in agriculture and horticulture. This fact is particularly surprising in light of the fact that most of these herbicides are known to affect photosynthesis in plants, whereas yeast cells are devoid of photosynthetic activity.

Many of the above-mentioned herbicides are characterized chemically by the formula Ar—N(R$_1$)—CO—R$_2$, where Ar is a radical containing an aromatic ring. The Ar radical may be a benzene or an alkylbenzene ring which optionally carries one or several polar substituents, such as a halogen atom or a methoxy or trifluoromethyl radical. The Ar radical may also be a heterocyclic ring, such as benzothiazol or thiadiazol. In the formula, R$_1$ is generally a hydrogen atom, but it may also be an alkyl or a hydroxyl group. R$_2$ may be an alkyl, a cycloalkyl or a alkenyl radical, as is the case for a class of herbicides of the carboxyaniline type, where Ar is a phenyl radical which may be substituted. These herbicides are known to have an inhibiting action on photosynthesis. A typical example is 3',4'-dichloropropioanilide, also known as "Propanil" (see THE PESTICIDE MANUAL 446, BCPC (6th ed. C. R. Worthing 1979)).

R$_2$ may also be an alkoxy group, in which case the herbicides are of the carbamate type. A typical example is methyl-3,4-dichlorophenylcarbamate, commonly called "Swep" (Id. at 569), which also had an effect on photosynthesis. Another example is isopropyl-N-(3-chlorphenyl)carbamate, better known as "Chlorpropham" (Id. at 118).

R$_2$ may in addition be an alkylamino, cycloalkylamino, or alkoxyalkylamino group. Such herbicides generally are derived from urea, and they are also well known for their inhibition of photosynthesis. One example of this class of herbicides is 3-(3,4-dichlorophenyl)-1,1-dimethylurea, commonly called "Diuron" (Id. at 224). Typical examples of herbicides wherein Ar is a heterocyclic ring are 1-(2-benzothiazolyl)-3-methylurea, called benzothiazuron (Id. at 37) and 1-(5-tert-butyl-1,3,4-thiadiazol-2-yl)1,3-dimethylurea, called tebuthiuron (Id. at 495).

Another important family of herbicides which display a surprising inhibition of yeast growth is characterized chemically by the formula

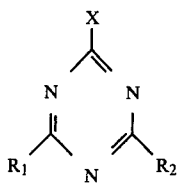

wherein
X may be a chloro, methoxy or methylthio radical,
R$_1$ and R$_2$ may be ethylamino and/or isopropylamino radicals.

Herbicides of this family are derived from S-triazine and also affect photosynthesis; they have considerable commercial importance. One of the most often used is 2-chloro-4-ethylamino-6-isopropylamino-1,3,5-triazone, better known as "Atrazine" (Id. at 21). Another is 2-chloro-4,6-bis(ethylamino)-1,3,5-triazine, also called "Simazine" (Id. at 474).

Other herbicides which do not correspond to the above-described general formulas may also be used according to the present invention. For example, 3-amino-1,2,4-triazole, commonly called amitrol, may be used in the present invention; this herbicide is known for its action on the biosynthesis of carotenoids.

Although the exact mechanism of action of these herbicides on yeast has not been studied in detail, it may be that many of them affect the respiratory function, given their differential effect on yeast growth in a medium wherein the only carbon source, e.g., glycerol, is a substitute for a respiration, as opposed to a medium containing a carbon source, such as glucose, which allows both fermentation and respiration.

In at least one case, a mutant of the yeast *Saccharomyces cerevisiae* which is intrinsically resistant to a herbicide (Diuron) has been isolated (see A. M. Colson et al., *Eur. J. Biochem.* 74: 721, 1977). However, the exclusively mitochondrial location of the genetic marker corresponding to the resistance trait makes the marker totally unsuitable for use in attempting to impart, by transformation, herbicide resistance to yeast in general. On the other hand, it is known that intrinsic resistance markers are usually recessive, which in principle makes them unsuitable for cloning for the purpose of conferring resistance. That this is the case for *Saccharomyces cerevisiae* (see J. R. Broach, THE MOLECULAR BIOLOGY OF THE YEAST SACCHAROMYCES CEREVISIAE-LIFE CYCLE AND INHERITANCE 723, Cold Spring Harbor Laboratory, (ed. J. N. Strathern, E. W. Jones, & J. R. Broach 1981)), has been confirmed in the only known report on the cloning of a recessive marker for intrinsic resistance to the antibiotic trichodermin in *Saccharomyces cerevisiae*, which resistance was not expressed in the transformant (see C. P. Hollenberg, *Curr. Top. Microbiol. Immunol.*, 96: 119, 1982).

As another important aspect of the present invention, it has been found that it is possible to isolate mutants of the yeast *Saccharomyces cerevisiae* which are intrinsically resistant to herbicide-type inhibitors such as those described above, and in which the genetic marker responsible for the resistance trait is semi-dominant and localized in the chromosomes of the nucleus. Such mutants have been obtained by the classical method of selection on a culture medium containing the herbicide of interest.

It has also been found, quite surprisingly, that these mutants are resistant not only to the herbicide by which they were selected, but also to other synthetic organic herbicide-type inhibitors. This feature consitutes an important property of the intrinsic resistance genes of the present invention.

As yet another important aspect of the present invention, it has also been found that the yeast *Saccharomyces cerevisiae* can acquire, by transformation with the above-described resistance gene, a multiple resistance phenotype similar to that of the original mutant strain, and that this transformation can be effected with genetic manipulation methods currently used for yeast.

Transforming a herbicide-sensitive yeast into a yeast which is resistant to at least one of the herbicides mentioned above can be carried out with any of the genes coding for intrinsic resistance to the herbicide, using any of several available autoreplicating vectors which are suitable for the yeast *Saccharomyces cerevisiae*. Illustrative examples of such known vectors include plasmids built by J. D. Beggs, designated pJDB 207, pJDB 219, and pJDB 248 (J. D. Beggs, 2 GENETIC ENGINEERING 125, (Academic Press ed. R. Williamson, 1981); by C. P. Hollenberg, designated pMP78 and pMP81 (C. P. Hollenberg, *Curr. Top. Microbiol. Immunol.* 96: 119, 1982); and by Fournier et al, as described in European patent application No. 11,562, the contents of which are incorporated herein by reference.

Yeasts transformed by one of the suitable plasmids, into which a resistance gene has been previously inserted in accordance with the present invention, may be cultivated for commercial purposes, e.g., for the industrial production of a polypeptide encoded by a gene inserted into the same plasmid as for the resistance gene, under conditions which ensure the genetic stability of the fermentation culture while avoiding the above-mentioned drawbacks inherent in the presently used methods for controlling genetic instability. Pursuant to the present invention, it is sufficient to add to the culture medium one of the growth inhibitors towards which the yeast has been made resistant by transformation, at a concentration such that only the transformants, and not phenotypical revertants which may appear during fermentation, can survive and multiply.

EXAMPLE 1

Isolation of a mutant of yeast *Saccharomyces cerevisiae* which is spontaneously resistant to herbicide-type growth inhibitors.

A yeast mutant designated D273-10B/A21/$D^R_{217}$ (hereinafter $DIU^R_{217}$), which is spontaneously herbicide-resistant, was isolated from the *Saccharomyces cerevisiae* strain D273-10B/A21 by selection on a glycerol medium to which Diuron has been added at a concentration of 100 $\mu M$. (The inhibition threshold of 75 $\mu M$ for this strain was previously determined experimentally for haploid as well as for diploid cells.) The nuclear localization of the resistance marker of $DIU^R_{217}$ was confirmed by analyzing the marker's mode of transmission to progeny derived by cross-breeding the mutant with a sensitive strain. Analysis of the tetrades revealed that the marker followed a segregation which was typically mendelian. The analysis of the resistance trait of heterozygous diploids derived from the aforementioned cross revealed the semi-dominant character of the resistance marker, in that the inhibition threshold for the diploids was about 100 $\mu M$ and that of the haploid mutant was about 150 $\mu M$.

$DIU^R_{217}$ was found to be resistant, not only to the herbicide which had been used to select for the mutant, but also towards other herbicides of the respiration inhibition type, such as

| | |
|---|---|
| atrazine | (threshold 2 mM, resistance 5 mM), |
| chlorpropham | (threshold 0.3 mM, resistance 1 mM), |
| chloroxuron | which is 3-4-(4-chlorophenosy)phenyl-1,1-dimethylurea (threshold 0.01 mM, resistance 0.05 mM), |
| monuron | which is 3-(4-chlorophenyl)-1,1-dimethylurea (threshold 0.5 mM, resistance 1.5 mM), |
| monolinuron | which is 3-(4-chlorophenyl)-1-methoxy-1-methylurea (threshold 1 mM, resistance 3 mM), |
| desmetryne | which is 2-isopropylamino-4-methylamino-6-methylthio-1,3,5-triazine (threshold 1 mM, resistance 5 mM), |
| metribuzine | which is 4-amino-6-tert-butyl-4,5-dihydro-3-methylthio-1,2,4-triazine-5-one (threshold 5 mM, resistance 50 mM), |
| and dinoseb | which is 2-sec-butyl-4,6-dinitrophenol (threshold 0.2 mM, resistance 0.4 mM). |

EXAMPLE 2

Cloning and expression of a gene encoding intrinsic resistance to herbicides in *Saccharomyces cerevisiae*

DNA was extracted and purified from a liquid culture of mutant $DIU^R_{217}$ and subjected to restriction by the enzyme Pst I. The resulting restriction fragments were inserted by in vitro recombination into the shuttle-plasmid pJDB207, which had been cleaved at a Pst I site located within the resistance marker to ampicillin. Strain HB101 of the bacterium *Escherichia coli* was transformed with the chimeric plasmids in order to establish a genomic bank for mutant $DIU^R_{217}$ in the form of a collection comprising some 100,000 clones of transformed *E. coli*, each clone containing one or more chimeric plasmids and displaying a sensitivity to ampicillin and a resistance to tetracycline.

A culture of *E. coli* was established, by inoculating a suitable medium with all the clones of the genomic bank, in order to amplify the chimeric plasmids contained therein. DNA was extracted from the culture, and the plasmids were then purified by isopycnic centrifugation on cesium chloride in the presence of ethidium bromide. The plasmids were used to transform the *Saccharomyces cerevisiae* strain AH22 according to a method described by A. Hinnen et al., *Proc. Natl. Acad. Sci., USA* 75: 1929, 1978). The resulting transformants were selected on a glucose medium free of leucine, and transformed clones which were Diuron resistant were thereafter derived by culturing the selected transformants on a glycerol medium to which Diuron had been added at a concentration of 100 $\mu M$.

That herbicide resistance of many clones obtained with the above-described method was attributable to the presence of one or more chimeric plasmids which carried the resistance marker derived from $DIU^R_{217}$, was confirmed by two different tests. First, each clone of the collection was cured in accordance with the Hollenberg method (see C. P. Hollenberg, *Curr. Top. Microbiol. Immunol.* 96: 119, 1982). It was then determined that many of the clones had, after curing, reverted to a phenotype which was both auxotrophic as regards to leucine and sensitive to Diuron; clones which did not satisfy this test were eliminated.

As a second test, DNA was extracted from a liquid culture which had been inoculated with one of the clones retained from the first test, and was used to transform the *E. coli* strain HB101 in order to establish a bank of plasmids of the retained clone. The resulting *E. coli* clones, hereinafter called "secondary" *E. coli* clones, were pooled in groups of 50 in order to carry out the inoculation of mixed cultures, from which plasmids were then extracted as described above. These plasmids were used to transform strain AH22 as previously described. By this method, a large number of Diuron resistant yeast clones, hereinafter called "secondary" yeast clones, were obtained with a very high frequency.

Among all the chimeric plasmids represented in the bank of secondary *E. coli* clones, a search was made to discover the plasmid which was responsible for the observed resistance. To this end, the above-described procedure was repeated, so that plasmids were purified from each of the individual clones constituting the group of 50 plasmids fulfilling the test of secondary transformation of yeast. It was observed by electrophoresis that a wide variety of plasmids were thus obtained, the plasmids showing important differences, on the one hand, as to the size of the inserted yeast DNA fragments and, on the other hand, as to their respective restriction profiles. The different plasmids were grouped into about ten distinct classes, each displaying the heteroplasmidic character of the primary yeast transformation. (The different classes of plasmids are thought to result from the multiple occurrence of the initial transformation event, and from the further possibility of recombination events.)

Clones which were representative of each of the classes were identified, and from each clone was derived a preparation of plasmid which was individually purified as described above. One of them, called pDIU202, showed a capability of conferring, by transformation of strain AH22 in accordance with the above-described methods, a phenotype which was both prototrophic as to leucine and resistant to the same herbicides for which the original mutant $DIU^R_{217}$ was resistant. The size of the fragment inserted into plasmid pDIU202 was estimated by electrophoresis to be about 1.5 Kb in length.

A strain of E. coli transformed by plasmid pDIU202 was filed on May 4, 1983, under No. LMB 83.07 (=CBS 396.83) in Centraalbureau voor Schimmelcultures, Oosterstraat 1, 3740 AG Baarn, Netherlands.

EXAMPLE 3

Process for the selective culture of Saccharomyces cerevisiae converted by a plasmid containing a gene encoding intrinsic resistance to herbicides, wherein the genetic stability of the population is ensured.

A liquid culture of the AH22 strain transformed by means of plasmid pDIU202 as described in Example 2 was grown at 30° C. under constant stirring in an erlenmeyer flask containing 100 ml of a complete glycerol medium, to which medium Diuron was added to a final concentration of 100 μM. During the exponential phase of the resulting culture, an aliquot was taken therefrom and used to inoculate a similar culture medium, using a dilution ratio such that the second culture was immediately in the exponential phase of growth. This procedure was repeated for successive cultures during an observation period of 300 hours, which corresponds to 132 generations.

Samples were taken from the successive cultures, at intervals corresponding to the following numbers of generations: 0, 8, 15, 25, 43, 57, 68, 78, 91, 110, and 132. For each sample, the cells were spread on Petri dishes containing a solid, complete glycerol medium in order to obtain isolated colonies. Each time, 50 of the colonies were sub-cultured according to the sterile toothpick technique on a set of 4 Petri dishes containing, respectively, the following solid media:
1. complete glycerol
2. complete glycerol and Diuron (100 μM)
3. minimum glycerol and histidine
4. minimum glucose and histidine The colonies which grew on each of these Petri dishes were counted. In all cases, it was observed that every one of the 50 sub-cultured colonies grew on each of the aforementioned Petri dishes. These results confirmed that no phenotypic revertant had appeared, either for leucine auxotrophy or for the Diuron sensitivity, over 132 culture generations, during which a positive force of selection had been exerted by the presence of Diuron.

This remarkable genetic stability of the population of yeast cells transformed by plasmid pDIU202 is quite unexpected in light of reported observations indicative of the state of the art (see, e.g., N. Gunge, Ann. Rev. Microbiol. 37: 253, 1983) for yeasts converted by means of autoreplicative plasmids of the YEp (Yeast Episomal plasmids) class, to which plasmid pDIU202 belongs. With such autoreplicative plasmids, it is well known that phenotype reversion frequencies of about 12 or more per generation are observed, even if a selection pressure is exerted. (In all previously reported cases, the selection was of the negative type.) By way of example, the following reports are cited, all concerning yeast cells which were transformed by means of the signated plasmids, and which displayed genetic instability after transformation:

pleu 1.4 et pleu 2.6.
(J. B. Hicks, A. Hinnen & G. R. Fink, Cold Spring Harbor Symposium on Quantitative Biology 43: 1305, 1979)

pJDB110, pJDB207, pJDB209, pJDB210 et pJDB211
(J. D. Beggs, A. Benzon Symposium 16, 383, 1981)

pJDB219
(J. D. Beggs, A. Benzon Symposium, 16 383, 1981; C. P. Hollenberg, Curr. Top. Microbiol. Immunol. 96: 119, Bacteriol. 141: 413, 1980; R. M. Walsely, D. C. J. Garnder & S. G. Oliver, Mol. Gen. Genet. 192: 361, 1983)

(C. Gerbaud, P. Fournier, H. Blanc, M. Aigle, H. Heslot & M. Guerineau, Gene 5: 233, 1979)

YEp13
(C. L. Hsiao & J. Carbon, Proc. Natl. Acad. Sci., USA 78: 3760, 1981)

YEp4
(K. Struhl, D. T. Stinchcomb, S. Scherer & R. W. Davie, Proc. Natl. Acad. Sci., USA 76: 1035, 1979)

In order to confirm the existence of genetic instability in a control-culture of transformed yeast cells, the pJDB207 plasmid used in Example 2 above was employed, since it is identical to pDIU202 except that the former lacks the 1.5 Kb fragment responsible for resistance to Diuron; thus, pJDB207 is unable to sustain a positive selection pressure by addition of Diuron to the culture medium. Liquid cultures of Saccharomyces cerevisiae strain AH22 which were previously transformed with plasmid pJDB207 were prepared in accordance with the procedure described above, except that Diuron was not added to the medium and the samples were taken at intervals corresponding to the following generations: 0, 13, 26, 38, 51 and 66. Revertants displaying auxotrophy to leucine were observed as early as the 26th generation (2%), and with an increasing frequency thereafter, as it can be seen from the following results:

After 38 generations—4%
After 51 generations—6%
After 66 generations—20%

These results clearly show that the process of the present invention for the selective culture of transformed yeast cells guarantees the genetic stability of a transformed yeast population by means of a positive selection pressure exerted via a herbicide in favor of cells containing a plasmid which itself contains a gene coding for intrinsic resistance towards the herbicide.

What is claimed is:

1. A recombinant yeast cloning vector comprising (i) plasmid capable of transforming a yeast cell and (ii) DNA comprising a gene coding for resistance to at least the organic herbicide 3-(3,4-dichlorophenyl)-1,1-dimethylurea, wherein said gene is a nuclear determinant in yeast.

2. A cloning vector according to claim 1, wherein said DNA is derived from at least one yeast mutant selected for by culturing a parental yeast strain on a culture medium containing said organic herbicide.

3. A cloning vector according to claim 2, wherein said DNA codes for resistance to said organic herbicide contained in said culture medium and at least one other organic herbicide.

4. A cloning vector according to claim 2, wherein said gene is semi-dominant in said yeast mutant.

5. A cloning vector according to claim 4, wherein said DNA is about 1.5 kilobases in length.

6. A cloning vector according to claim 5, said cloning vector comprising plasmid pDIU202.

7. A cloning vector according to claim 1, wherein said plasmid comprises a yeast episomal plasmid.

8. A cloning vector according to claim 1, wherein said plasmid is selected from the group consisting of pJDB207, pJDB219, pJDB248, pMP78 and pMP81.

9. A cloning vector according to claim 1, wherein said gene also codes for resistance to a herbicide, other than 3-(3,4-dichlorophenyl)-1,1-dimethylurea, that is characterized by the formula $$Ar-N(R_1)-CO-R_2$$

wherein
Ar denotes a radical comprising an aromatic ring;
$R_1$ denotes one selected from the group consisting of a hydrogen, a methyl radical, and a hydroxyl radical; and
$R_2$ denotes a radical selected from the group consisting of an alkyl, a cycloalkyl, an alkenyl, an alkylamino, a cycloalkylamino, an alkoxyalkylamino, and an alkoxy.

10. A cloning vector according to claim 9, wherein $R_2$ denotes a radical selected from the group consisting of a methylamino, a dimethylamino, and a methoxymethylamino.

11. A cloning vector according to claim 9, wherein Ar denotes a radical comprising a benzene ring which is substituted or unsubstituted.

12. A cloning vector according to claim 11, wherein Ar denotes a phenyl radical comprising 1 or 2 substituents selected from the group consisting of a halogen atom, an alkyl radical, a methoxy radical, and a trifluoromethyl radical.

13. A cloning vector according to claim 9, wherein said herbicide is isopropyl-N-(3-chlorophenyl)carbamate.

14. A cloning vector according to claim 1, wherein said gene also codes for resistance to a herbicide, other than 3-(3,4-dichlorophenyl)-1,1-dimethylurea, that is characterized by the formula

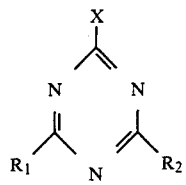

wherein
X denotes a radical selected from the group consisting of a chloro, a methoxy, and a methylthio; and
$R_1$ and $R_2$ separately denote a radical selected from the group consisting of a ethylamino and an isopropylamino.

15. A cloning vector according to claim 14, wherein said herbicide comprises 2-chloro-4-ethylamino-6-isopropylamino-1,3,5-triazine.

16. A cloning vector according to claim 14, wherein said herbicide comprises 2-chloro-4,6-bis(ethylamino)-1,3,5-triazine.

17. A cloning vector according to claim 1, wherein said gene also codes for resistance to the herbicide 3-amino-1,2,4-triazole.

18. A yeast culture comprised of yeast transformants containing a yeast cloning vector comprising (i) a plasmid capable transforming a yeast cell and (ii) DNA comprising a gene coding for resistance to at least the organic herbicide 3-(3,4-dichlorophenyl)-1,1-dimethylurea wherein said gene is a nuclear determinant in yeast.

19. A yeast culture according to claim 18, wherein said transformants comprise transformed cells of yeast strain AH22 which contain said cloning vector.

20. A yeast culture according to claim 19, wherein said cloning vector comprises plasmid pDIU202.

21. A process for the culturing of yeast, comprising the step of maintaining a yeast culture comprised of yeast transformants containing a yeast cloning vector, said vector comprising (i) a plasmid capable of autonomous replication in a yeast cell and (ii) DNA coding for resistance to at least the organic herbicide 2-(3,4-dichlorophenyl)-1,1-dimethylurea on a growth medium which comprises, as the sole carbon source for said culture, a substrate for respiration, said medium containing an amount of an organic herbicide to which said transformants are resistant which is sufficient to keep said culture substantially free of revertants.

22. A process according to claim 21, wherein said substrate for respiration comprises glycerol.

23. A process according to claim 22, wherein said cloning vector comprises plasmid pDIU202.

24. A process according to claim 21, wherein said organic herbicide comprises 3-(3,4-dichlorophenyl)-1,1-dimethylurea.

25. A cloning vector according to claim 1, wherein said gene is localized on a nuclear chromosome in *Saccharomyces cerevisiae*.

26. A cloning vector according to claim 1, wherein said gene also codes for resistance to a herbicide of the respiration inhibition type other than 3-(3,4-dichlorophenyl)-1,1-dimethylurea.

27. A cloning vector according to claim 26, wherein said gene also codes for resistance to a herbicide selected from the group consisting of atrazine, chlorpropham, chloroxuron, monuron, monolinuron, desmetryne, metribuzine and dinoseb.

28. A yeast culture according to claim 18, wherein said gene is localized on a nuclear chromosome in *Saccharomyces cerevisiae*.

29. A yeast culture according to claim 18, wherein said gene also codes for resistance to a herbicide of the respiration inhibition type other than 3-(3,4-dichlorophenyl)-1,1-dimethylurea.

30. A yeast culture according to claim 29, wherein said gene also codes for resistance to a herbicide selected from the group consisting of atrazine, chlorpropham, chloroxuron, monuron, monolinuron, desmetryne, metribuzine and dinoseb.

* * * * *